United States Patent [19]

Kobayashi et al.

[11] Patent Number: 5,556,642
[45] Date of Patent: Sep. 17, 1996

[54] METHOD FOR PRODUCING SUSTAINED RELEASE MICROSPHERE PREPARATION

[75] Inventors: Masao Kobayashi, Kyoto; Yukiko Nishioka, Toyonaka; Takehiko Suzuki, Toyono-gun; Yashuhisa Matsukawa, Osaka, all of Japan

[73] Assignee: Tanabe Seiyaku Co., Ltd., Osaka, Japan

[21] Appl. No.: 89,194

[22] Filed: Jul. 12, 1993

[30] Foreign Application Priority Data

Jul. 16, 1992 [JP] Japan ................................. 4-189181

[51] Int. Cl.⁶ ................................ A61K 9/48; A61K 9/14; A61K 9/16; A61K 9/50
[52] U.S. Cl. .................... 424/502; 424/451; 424/489; 424/497; 424/498; 424/501; 514/963; 428/402.21; 264/4.1; 264/4.6
[58] Field of Search ................................. 424/451, 489, 424/497, 498, 501, 502; 514/963; 428/402.21; 264/4.1, 4.6

[56] References Cited

U.S. PATENT DOCUMENTS

| 3,976,071 | 8/1976 | Sadek | 424/425 |
|---|---|---|---|
| 4,384,975 | 5/1983 | Fong | 264/4.6 |
| 4,479,911 | 10/1984 | Fong | 264/4.6 |
| 4,933,105 | 6/1990 | Fong | 264/4.6 |

FOREIGN PATENT DOCUMENTS

| 058481 | 1/1982 | European Pat. Off. . |
|---|---|---|
| 052510 | 6/1982 | European Pat. Off. . |
| 133988 | 8/1984 | European Pat. Off. . |
| 145240 | 6/1985 | European Pat. Off. . |
| 190833 | 8/1986 | European Pat. Off. . |
| 0263490 | 4/1988 | European Pat. Off. . |
| 315875 | 11/1988 | European Pat. Off. . |
| 330180 | 8/1989 | European Pat. Off. . |
| 461630 | 6/1991 | European Pat. Off. . |
| 525966 | 3/1992 | European Pat. Off. . |

OTHER PUBLICATIONS

Hiroshi Yuasa et al, Application of the Solid Dispersion Method to Controlled Release of Medicine. I. Controlled Release of Water Soluble Medicine by Using Solid Dispersion, Chem. Pharm. Bull. 39(2) 465–467 (1991).

*Primary Examiner*—Carlos A. Azpuru
*Attorney, Agent, or Firm*—Finnegan, Henderson, Farabow, Garrett & Dunner, L.L.P.

[57] ABSTRACT

A method for producing sustained release microsphere preparation for water-soluble medicament, which has high incorporation efficiency of the medicament and low initial burst, which comprises dissolving water-soluble pharmaceutical active ingredient and water-insoluble biodegradable polymer in one or two solvents in which both can dissolve, removing the solvent to give a solid dispersion having the water-soluble pharmaceutical active ingredient dispersed into said biodegradable polymer at molecular level, and further, dissolving said solid dispersion in an organic solvent being water-immiscible and having a boiling point of below 100° C., and adding the resulting oil phase into an aqueous phase containing emulsifying agent to give O/W emulsion, and followed by removing the organic solvent from the oil phase of the resulting emulsion.

6 Claims, 2 Drawing Sheets

3

METHOD FOR PRODUCING SUSTAINED RELEASE MICROSPHERE PREPARATION

The present invention relates to a solid dispersion wherein a water-soluble pharmaceutically active ingredient is dispersed into a biodegradable polymer, a process for preparing the same, and a method for producing a sustained release microsphere preparation using the same.

PRIOR ART

Hitherto, there have been known some microspheres using biodegradable polymer, which can effectively sustain a pharmacological activity of a biologically active substance for a long period of time, and there have also been known various methods for producing thereof. For instance, Japanese Patent First Publication (Kokai) No. 11851/1982 discloses a microcapsule-type microsphere preparation prepared by a phase separation technique using coacervation-inducing agents. However, during the process disclosed in said Japanese Patent First Publication, aggregation of particles easily happens, and since mineral oil or vegetable oil is used therein as a dispersion solvent, there are some difficulties in separation and washing of the resulting microspheres. Moreover, the resulting microsphere are often hollow, and hence, it is difficult to obtain microspheres having a certain and constant quality.

In order to overcome the above mentioned defects, there are disclosed several methods for producing microspheres by solvent evaporation method, for example, Japanese Patent First Publication (Kokai) No. 100516/1985 and Japanese Patent First Publication (Kokai) No. 201816/1987 disclose a technique using a water in oil in water (W/O/W) emulsion, Japanese Patent First Publication (Kokai) No. 216918/1989 discloses one with an oil in oil (O/O) emulsion, and Japanese Patent First Publication (Kokai) No. 91325/1988 and Japanese Patent First Publication (Kokai) No. 46115/1992 disclose the one with an oil in water (O/W) emulsion.

In general, since most of biologically active substances, which need a sustained release property, are water-soluble, the preparation of microspheres from W/O emulsion or from O/O emulsion using the solvent evaporation method works best to incorporate a biologically active substance into microspheres. However, it is difficult to remove completely the solvents from microspheres, and there are many other problems, for example, safety of operation, or environmental problems. Besides, there is used a mineral oil or vegetable oil as an external oil phase in W/O emulsion and O/O emulsion, and hence, it is difficult to collect or to wash the resulting microspheres, and the remaining oil in microspheres is a significant problem.

On the other hand, in the above mentioned W/O/W method or O/W method, the external phase is an aqueous solution, and hence, there is no problem as mentioned in W/O method or O/O method. However, the pharmaceutical active ingredient in oil phase often dissolves out into the external aqueous solution so that the incorporation efficiency of the active ingredient into microspheres becomes low.

In order to overcome the above mentioned defects, there are disclosed W/O/W methods in Japanese Patent First Publication (Kokai) No. 10051 6/1985 and Japanese Patent First Publication (Kokai) No. 201816/1987, which comprises dissolving gelatin into the internal aqueous phase. However, the emulsification process must be repeated twice in W/O/W method, and as a result, the proceedings are complicated so that it is necessary to define strictly the conditions for each step in order to obtain microspheres having a certain and constant properties. In addition, this method cannot be effectively applied to every medicament, and since such additives as gelatin, arginine, gum arabic, etc., are used to sustain the medicament in the phase in this method, it is also important and significant problem to sterilize these additives and further to avoid pyrogenation of these additives Under the above mentioned circumstances, it has been desired to produce microspheres from O/W emulsion, which can also incorporate a water-soluble pharmaceutical active ingredient at a high rate in viewpoint of operation efficiency and safety.

However, the conventional method for producing microspheres from O/W emulsion, i.e. the method which comprises dispersing a medicament powder into an oil phase to give an O/W emulsion, followed by removing solvents by the solvent evaporation method, or dissolving a water-soluble medicament in an oil phase containing a water-miscible organic solvent to give an O/W emulsion, followed by removing solvents by the solvent evaporation method, have some defects. For example, there is burst-effect (rapid release of medicament within a short period of time), or suitable species of medicaments and biodegradable polymer are limited. In O/W method wherein the medicament crystals are dispersed into oil phase, the water-soluble medicament is not dissolved in the oil phase (i.e. the polymer phase), and hence, the medicament exists heterogeneously in the oil phase in the form of crystalline particles. As a result, the medicament leaks out into the external aqueous solution in the emulsification step, which causes extremely low incorporation efficiency of the medicament into the microspheres. Besides, crystals of the medicament make pores on the surface of the microspheres being solidifying during emulsification, which often leads to an initial burst as mentioned above.

BRIEF DESCRIPTION OF THE INVENTION

An object of the present invention is to provide a solid dispersion which comprises a water-soluble pharmaceutical active ingredient homogeneously dispersed in a biodegradable polymer. Another object of the present invention is to provide a method for preparing said solid dispersion. A further object of the present invention is to provide a method for producing a sustained release microsphere preparation using said solid dispersion.

DETAILED DESCRIPTION OF THE INVENTION

Figure 1:
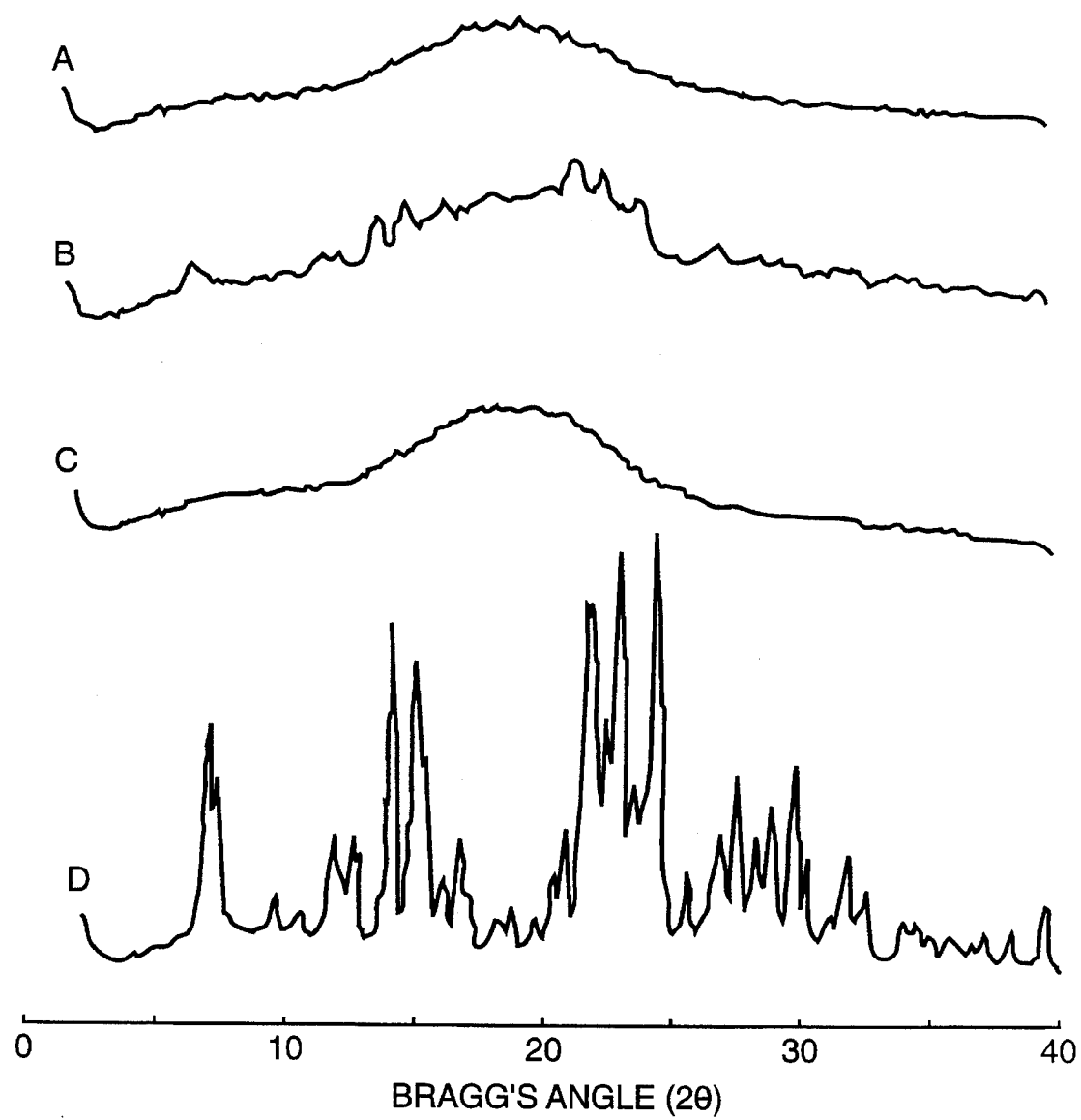
FIG. 1 shows X-ray powder diffraction patterns of Solid Dispersion 1 prepared in Example 1 and the other starting materials.

The present inventors have intensively studied, and have found that before emulsification for producing microspheres, there is obtained a solid dispersion containing a water-soluble pharmaceutical active ingredient dispersed in a biodegradable polymer homogeneously by dissolving a biodegradable polymer and a water-soluble pharmaceutical active ingredient in one or more solvents in which they both dissolve, and followed by removing the solvents therefrom, and further found that by using said solid dispersion, there is obtained a sustained release microsphere preparation having a high incorporation efficiency of the medicament with low initial burst, that is, by dissolving said solid dispersion thus obtained in an organic solvent (said solvent being water-immiscible and having a boiling point of below 100° C.), emulsifying the resulting solution (oil phase) into an aqueous phase to give an oil in water (O/W) emulsion, and removing the organic solvent from the oil phase of the resulting emulsion.

The method of the present invention can be applied to water-soluble medicaments which cannot dissolve in water-immiscible organic solvents such as methylene chloride, chloroform, carbon tetrachloride, dichloroethane, etc., for example, thyrotropin-releasing hormone (TRH), luteinizing hormone releasing hormone (LH-RH), calcitonin, 1-methyl-4,5-dihydroorotyl-histidyl-prolinamide, nicotinamide, and the like. Most of these medicaments are soluble not only in water but also in acetonitrile, ethanol, methanol, 1- or 2-propanol, 1- or t-butanol, and the like. Accordingly, among these solvents, a solvent which can dissolve also a biodegradable polymer is used for preparing a solid dispersion of the present invention. In addition, when a biodegradable polymer cannot dissolve in one of these solvents, a biodegradable polymer and a water-soluble medicament are dissolved in a mixture of the above mentioned solvents and a water-immiscible organic solvent to give effectively a solid dispersion of the present invention.

As mentioned above, any medicament which is not soluble in water-immiscible organic solvents (e.g. methylene chloride, chloroform, carbon tetrachloride, dichloroethane, etc.) but be water-soluble, can be used in the microsphere preparation of the present invention, for example, anticancer agents, antibiotics, antipyretics, analgesics, immune stimulator, immune suppressive agents, antiinflammatory agents, antiepileptics, agents for improving cerebral disorders, antihistamic agents, hypotensive diuretics, antidiabetics, muscle relaxant, anti-ulcer agents, antidepressant, antiallergic agents, cardiotonics, antiarrhythmic agents, vasodilators, anticoagulants, narcotic antagonists, hemostatics, antitubercular agents, hormones, and the like.

The biodegradable polymer, which is used as a polymeric matrix for the microspheres of the present invention, may be any polymer which does not show any biological activities and are easily decomposed and disappears in the living body, but it is more effective to use a biodegradable polymer which dissolves in both water-immiscible organic solvents (e.g. methylene chloride, chloroform, carbon tetrachloride, dichloroethane, etc.) and water-miscible organic solvents (e.g. acetonitrile, acetone, etc.). Suitable examples of the biodegradable polymer are hydroxy acid polyesters, for example, polymers of lactic acid, glycolic acid and hydroxybutyric acid, or copolymer thereof, or a mixture thereof. Suitable examples of such biodegradable polymers include polylactic acid, polyglycolic acid, polyhydroxybutyric acid, poly γ-caprolactone, poly δ-valerolactone, lactic acid-glycolic acid copolymer, etc. Particularly, polylactic acid and lactic acid-glycolic acid copolymer (hereinafter referred to as "copoly(lactic/glycolic) acid"), having a molecular weight of 5,000 to 500,000, are more preferable. Besides, these polymers can be used either alone or in the form of a mixture of two or more thereof.

The content of a water-soluble medicament is not specified, and varies depending on the types of the medicaments to be used, the desired pharmacological effects, and the releasing time to be required, but it is preferably in the range of about 0.1–30% w/w, more preferably in the range of about 1 to 20% w/w to the biodegradable polymer.

The solvent used for preparation of the present solid dispersion may be water or any organic solvent alone, or a mixture of two or more, and is selected depending on the types of the biodegradable polymer and water-soluble medicaments to be used, but the most suitable solvent is one which can dissolve both the water-soluble medicament and biodegradable polymer, and can produce a solid dispersion when drying. When polylactic acid or copoly(lactic/glycolic) acid is used as a biodegradable polymer, the solvent for dissolving the polymer may be either water-immiscible organic solvents (e.g. methylene chloride, chloroform, carbon tetrachloride, dichloroethane, etc.) or water-miscible organic solvents (e.g. acetonitrile, acetone, etc.). However, as mentioned above, in order to obtain a desired solid dispersion, it is necessary for said solvent to dissolve both the water-soluble medicament and biodegradable polymer. Accordingly, when a solvent in which both a water-soluble medicament and biodegradable polymer are soluble is used, a desired solid dispersion is easily obtained by using said solvent alone. However, when one of the above-mentioned water-immiscible organic solvents is used for dissolving a biodegradable polymer, the water-soluble medicament has often difficulty in dissolving therein. In such a case, it is effective to add an organic solvent which is a water-miscible and is also miscible with the above mentioned water-immiscible organic solvent (e.g. acetonitrile, ethanol, methanol, 1- or 2-propanol, 1- or t-butanol, etc.) into the mixture for preparing a solid dispersion. When two or more of the organic solvents are used together, it is preferable to use solvents of which boiling points are not much different but about the same. The mixing ratio of these solvents varies depending on the types and the amount of the water-soluble medicament and biodegradable polymer to be dissolved, but it is determined so that both components can dissolve therein.

When preparing a solid dispersion of the present invention, it is also effective to add synthetic or natural polymers (e.g. polyvinylpyrrolidone, gelatin, etc.), surfactants (e.g. polyoxyethylene hydrogenated castor oil, etc.), polyhydric alcohols (e.g. polyethylene glycol, etc.), sugars, amino acids, peptides, fats and oils, etc. into a water-soluble medicament and biodegradable polymer so as to improve the solubility of the water-soluble medicament and biodegradable polymer and to control the industrial efficiency and dissolution pattern and rate of the microspheres of the present invention.

The desired solid dispersion is obtained by removing these solvents by evaporation, for example, by heating the mixture under reduced pressure in a closed system, or by spray-drying, and the like. In this case, it is suggested to equip an apparatus for recovering all organic solvents to be removed for protection of the earth environment.

The organic solvent, which is used for dissolving the solid dispersion, may be any organic solvent which is water-immiscible and has a boiling point of below 100° C., for example, methylene chloride, chloroform, carbon tetrachloride, dichloroethane, and the like. Particularly, when polylactic acid or copoly(lactic/glycolic) acid is used as a biodegradable polymer, methylene chloride is preferable.

Subsequently, the oil phase thus obtained is emulsified into an aqueous solution for emulsification to give an oil in water (O/W) emulsion. To the aqueous solution used in this step is preferably added a emulsifying agent in order to increase the emulsification efficiency. The emulsifying agent may be any conventional one, for example, polyhydric alcohols (e.g. polyvinyl alcohol, polyethylene glycol, etc.), surfactants, polysaccharides (e.g. chitosan, etc.), gelatin, gum arabic, and the like. The emulsifying agent is used in an amount of 0.01 to 10% w/v, preferably 0.1 to 2 % w/v.

The emulsification procedure is carried out by a conventional method, for example, by using stirrer with propeller, turbine impeller emulsifier, ultrasonic dispersion mixer, high-pressure emulsifier, and the like.

The subsequent removal of the organic solvent from the oil phase of the emulsion thus obtained can be conducted by the conventional method (e.g. the solvent evaporation method).

For example, the solvent removal can be carried out by stirring the emulsion under heating or in vacuo. Further, it is preferable to recover the organic solvent to be removed. Since the heating rate, rate of stirring and degree of agitation in heat-method, and the rate of reducing pressure in vacuo-method affect the yield and the quality of the desired microspheres, it is necessary to define and control suitable conditions.

The microspheres thus obtained can be collected by centrifugation, filtration, etc., and washed by distilled water, and the moisture therein is removed by drying in air or lyophilization, etc., to give the microsphere preparation of the present invention.

The average particle size of the microsphere preparation of the present invention is in the range of about 1 to 100 μm.

EXAMPLES

The present invention is illustrated in more detail by the following Examples, Reference Examples and Experiments, but should not be construed to be limited thereto.

Example 1

A copoly(lactic/glycolic) acid copolymer (50:50, molecular weight; about 20,000, referred to as PLGA 5020, 900 mg) and 1-methyl-4,5-dihydroorotyl-histidyl-prolinamide (100 mg), which is a TRH derivative, are dissolved in a mixture of ethanol (1 ml) and methylene chloride (2 ml), and the mixture is evaporated to remove the organic solvents with Speed Vac Concentrator (manufactured by SAVANT CO., LTD.) to give a solid dispersion (referred to as Solid Dispersion 1).

Solid Dispersion 1 is dissolved in methylene chloride (1.5 ml), and this organic solution is emulsified into a 0.5% aqueous polyvinyl alcohol solution (400 ml) at 15° C., with Polytron Homogenizer (manufactured by Kinematica Co., Ltd.) at 10,000 rpm. for two minutes to give an oil in water (O/W) emulsion, which is subjected to removal of solvent by warming from 15° C. to 30° C. taking over a period of three hours, while stirring the mixture at 400 rpm with a paddle having four wings, to give microspheres. The microspheres are collected by centrifugation, washed three times with distilled water, and subjected to lyophilization to remove the moisture. The microspheres thus obtained have average molecular size of about 50 μm, and the most thereof have a particle size of below 100 μm (Preparation 1).

Example 2

PLGA 5020 (900 mg) and 1-methyl-4,5-dihydroorotyl-histidyl-prolinamide (100 mg) are dissolved in a mixture of acetonitrile (5 ml) and ethanol (1 ml), and the mixture is evaporated with Speed Vac Concentrator (manufactured by SAVANT CO., LTD.) to remove the organic solvents to give a solid dispersion (Solid Dispersion 2), which is dissolved in chloroform (1.5 ml), and the organic solution is emulsified into a 0.5% aqueous polyvinyl alcohol solution (400 ml) at 15° C. The resulting emulsion is treated in the same manner as in Example 1 to give microspheres (Preparation 2).

Example 3

PLGA 5020 (900 mg) and TRH (100 mg) are dissolved in a mixture of acetonitrile (5 ml) and ethanol (1 ml), and the mixture is evaporated with Speed Vac Concentrator (manufactured by SAVANT CO., LTD.) to remove the organic solvents to give a solid dispersion (Solid Dispersion 3), which is dissolved in methylene chloride (1.5 ml), and the organic solution is emulsified into a 0.5 % aqueous polyvinyl alcohol solution (400 ml) at 15° C. The resulting emulsion is treated in the same manner as in Example 1 to give microspheres (Preparation 3).

Example 4

PLGA 5020 (900 mg) and LH-RH (50 mg) are dissolved with warming in a mixture of acetonitrile (5 ml) and ethanol (3 ml), and the mixture is evaporated with Speed Vac Concentrator (manufactured by SAVANT CO., LTD.) to remove the organic solvents to give a solid dispersion (Solid Dispersion 4), which is dissolved in methylene chloride (1.5 ml). This organic solution is treated in the same manner as in Example 1 to give microspheres (Preparation 4).

Example 5

PLGA 5020 (900 mg) and 8-hydroxy-5-[(1R)-1-hydroxy-2-[N-((1R)-2-(p-methoxyphenyl)-1-methylethyl)amino]ethyl]-carbostyril hydrochloride (100 mg) are dissolved in a mixture of acetonitrile (5 ml), ethanol (1 ml) and water (0.5 ml), and the mixture is evaporated with Speed Vac Concentrator (manufactured by SAVANT CO., LTD.) to remove the organic solvents to give a solid dispersion (Solid Dispersion 5), which is dissolved in methylene chloride (1.5 ml). This organic solution is treated in the same manner as in Example 1 to give microspheres (Preparation 5).

Example 6

PLGA 5020 (700 mg), TRH (100 mg) and polyvinylpyrrolidone (200 mg) are dissolved in acetonitrile (100 ml), and the mixture is subjected to spray-drying to remove the acetonitrile to give a solid dispersion (Solid Dispersion 6), which is dissolved in chloroform (1.5 ml). The organic solution is treated in the same manner as in Example 1 to give microspheres (Preparation 6).

Example 7

PLGA 5020 (700 mg) and TRH (100 mg) are dissolved in acetonitrile (100 ml), and thereto is added a solution of gelatin (200 mg) in water (1 ml), and the mixture is well mixed. The mixture is subjected to spray-drying to remove the acetonitrile to give a solid dispersion (Solid Dispersion 7), which is dissolved in chloroform (1.5 ml). This organic solution is treated in the same manner as in Example 1 to give microspheres (Preparation 7).

Example 8

PLGA 5020 (700 mg), TRH (100 mg) and polyethylene glycol (200 mg) are dissolved in acetonitrile (100 ml), and the mixture is subjected to spray-drying to remove the acetonitrile to give a solid dispersion (Solid Dispersion 8), which is dissolved in chloroform (1.5 ml). This organic solution is treated in the same manner as in Example 1 to give microspheres (Preparation 8).

Example 9

PLGA 5020 (700 mg), TRH (100 mg) and polyoxyethylene hydrogenated castor oil (HCO-60, manufactured by Nikko Chemicals, 200 mg) are dissolved in acetonitrile (100 ml), and the mixture is evaporated by spray-drying to remove the acetonitrile to give a solid dispersion (Solid Dispersion 9), which is dissolved in chloroform (1.5 ml). This organic solution is treated in the same manner as in Example 1 to give microspheres (Preparation 9).

Example 10

PLGA 5020 (800 mg) and 1-methyl-4,5-dihydroorotyl-histidyl-prolinamide (200 mg) are dissolved in a mixture of methylene chloride (2 ml) and ethanol (1 ml), and the mixture is evaporated with Speed Vac Concentrator to remove the organic solvents to give a solid dispersion (Solid Dispersion 10), which is dissolved in methylene chloride (1.5 ml). This organic solution is emulsified into a 0.5% aqueous polyvinyl alcohol solution (400 ml) at 15° C., and treated in the same manner as in Example 1 to give microspheres (Preparation 10).

Reference Example 1

1-Methyl-4,5-dihydroorotyl-histidyl-prolinamide powder (100 mg), which is previously ground in an agate mortar, is added to a solution of PLGA 5020 (900 mg) in methylene chloride (1.5 ml), and the mixture is dispersed as much homogeneously as possible by applying ultrasonics thereto. This mixture is emulsified into a 0.5% aqueous polyvinyl alcohol solution (400 ml) at 15° C., and treated in the same manner as in Example 1 to give microspheres (Reference Preparation of Preparation 1).

Reference Example 2

1-Methyl-4,5-dihydroorotyl-histidyl-prolinamide powder (100 mg), which is previously ground in an agate mortar, is added to a solution of PLGA 5020 (900 mg) in chloroform (1.5 ml), and the mixture is dispersed as much homogeneously as possible by applying ultrasonics thereto. This mixture is treated in the same manner as in Reference Example 1 to give microspheres (Reference Preparation of Preparation 2).

Reference Example 3

TRH powder (100 mg), which is previously ground in an agate mortar, is added to a solution of PLGA 5020 (900 mg) in methylene chloride (1.5 ml), and the mixture is dispersed as much homogeneously as possible by applying ultrasonics thereto. This mixture is treated in the same manner as in Reference Example 1 to give microspheres (Reference Preparation of Preparation 3).

Reference Example 4

LH-RH powder (50 mg), which is previously ground in an agate mortar, is added to a solution of PLGA 5020 (900 mg) in methylene chloride (1.5 ml), and the mixture is dispersed as much homogeneously as possible by applying ultrasonics thereto. This mixture is treated in the same manner as in Reference Example 1 to give microspheres (Reference Preparation of Preparation 4).

Reference Example 5

8-Hydroxy-5-[(1R)-1-hydroxy-2-[N-((1R)-2-(p-methoxyphenyl)-1-methylethyl) amino]ethyl]carbostyril hydrochlorde powder (100 mg), which is previously ground in an agate mortar, is added to a solution of PLGA 5020 (900 mg) in methylene chloride (1.5 ml), and the mixture is dispersed as much homogeneously as possible by applying ultrasonics thereto. This mixture is treated in the same manner as in Reference Example 1 to give microspheres (Reference Preparation of Preparation 5).

Reference Example 6

1-Methyl-4,5-dihydroorotyl-histidyl-prolinamide powder (200 mg), which is previously ground in an agate mortar, is added to a solution of PLGA 5020 (800 mg) in methylene chloride (1.5 ml), and the mixture is dispersed as much homogeneously as possible by applying ultrasonics thereto. This mixture is emulsified into a 0.5% aqueous polyvinyl alcohol solution (400 ml) at 15° C., and treated in the same manner as in Reference Example 1 to give microspheres (Reference Preparation of Preparation 6).

Reference Examples 7–9

PLGA 5020 (800 mg) and 1-methyl-4,5-dihydroorotyl-histidyl-prolinamide powder (200 mg) are dissolved in a mixture of methylene chloride and ethanol (ratio; 1.35 ml:0.15 ml, 1.2 ml:0.3 ml, 1.05 ml:0.45 ml, respectively), and the mixture is emulsified into a 0.5% aqueous polyvinyl alcohol solution (400 ml) at 15° C., and treated in the same manner as in Example 1 to give microspheres (Reference Preparations of Preparation 10).

Experiment 1

Solid Dispersion 1, which is prepared in Example 1, was subjected to X-ray powder diffraction and differential scanning calorimeter (DSC) analysis. FIG. 1 shows the X-ray powder diffraction pattern. In FIG. 1, A is the pattern of Solid Dispersion of the present invention, B is the pattern of a physical mixture of copoly(lactic/glycolic) acid copolymer and 1-methyl-4,5-dihydroorotyl-histidyl-prolinamide, C is the pattern of copoly(lactic/glycolic) acid copolymer powder, and D is the pattern of 1-methyl-4,5-dihydroorotyl-histidyl-prolinamide powder, respectively. As shown in FIG. 1, the peak derived from the medicament disappeared from the pattern of Solid Dispersion 1. From the results of DSC analysis, the peak around the melting point of the medicament disappeared, which means that Solid Dispersion 1 was amorphous.

Furthermore, when Solid Dispersions 1–4 prepared in Examples 1–4 were dissolved in methylene chloride (or chloroform for Solid Dispersion 2), these solutions were all clear, and they did not precipitate at least for one hour, which is supposed to be a result of that the medicament and the biodegradable polymer form a solid dispersion. When Solid Dispersion 5 prepared in Example 5 was dissolved in methylene chloride in order to obtain an oil phase, the mixture was not clear but pale blue color, which means that there were produced sub-micron particles of the medicament. These sub-micron particles apparently had a smaller particle size than the original medicament.

The incorporation efficiency of the medicament of Preparations 1–5, and Reference Preparations thereof were measured by high performance liquid chromatography or UV spectrophotometry. The results are shown in Table 1.

TABLE 1

| | Incorporation Efficiency of Medicament | |
|---|---|---|
| | Preparation | Reference Preparation |
| 1 | 100.4% | 77.2% |
| 2 | 87.5% | 55.9% |
| 3 | 94.4% | 76.8% |
| 4 | 97.3% | 36.8% |
| 5 | 40.0% | 32.5% |

As is shown in Table 1, each Preparation showed higher incorporation efficiency than Reference Preparation thereof. Particularly Preparations 1–4, wherein solid dispersion was formed, showed extremely much higher incorporation efficiency than Reference Preparation thereof.

As a dissolution test, the following experiment was carried out. The microspheres (10 mg) obtained in Examples 2–4 were put into a test tube, and thereto was added an isotonic phosphate buffer (pH 7.4, 10 ml), and the mixture was shaken at 60 times/min, which continued for a certain period of time. The dissolution percentage of the active ingredient was measured. The results are shown in FIGS. 2–4.

Figure 2:
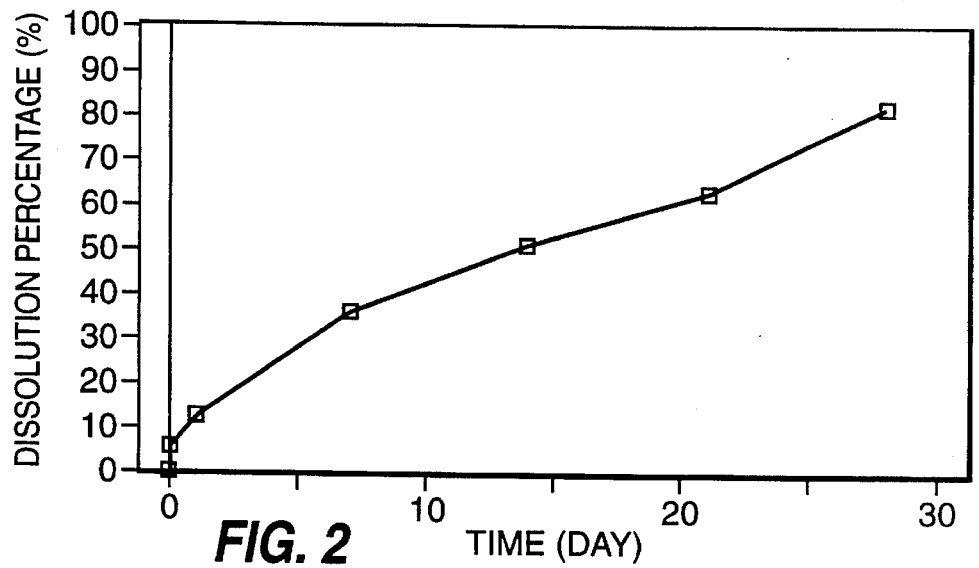
FIG. 2 shows the release profile of the active ingredient from Preparation 2 prepared in Example 2.
Figure 3:
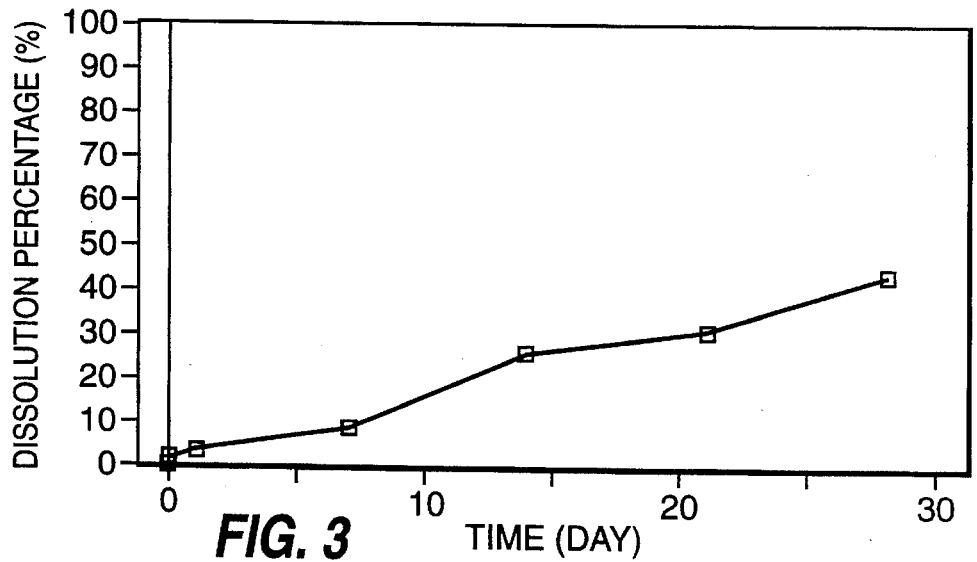
FIG. 3 shows the release profile of the active ingredient from Preparation 3 prepared in Example 3.
Figure 4:
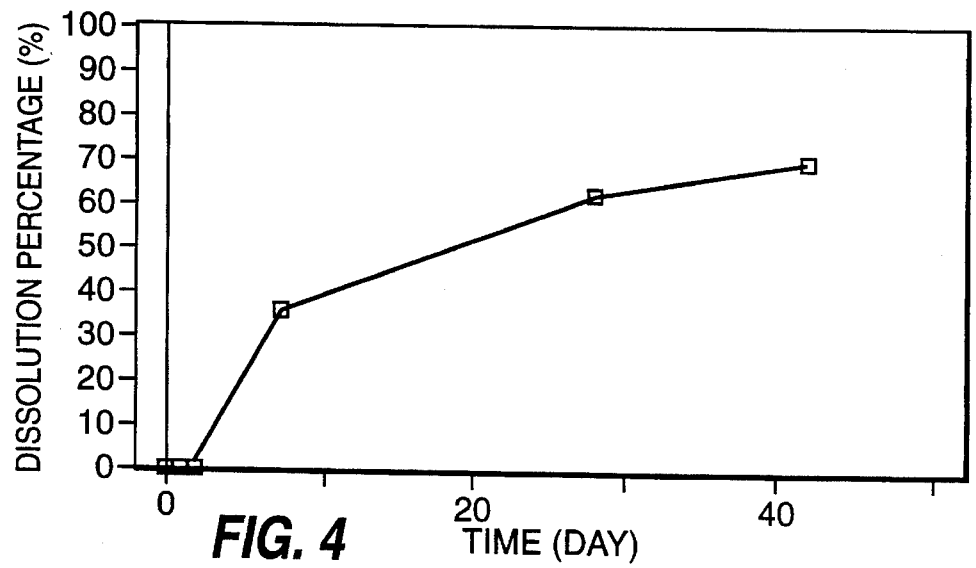
FIG. 4 shows the release profile of the active ingredient from Preparation 4 prepared in Example 4.

As is shown in FIGS. 2–4, the initial burst (the rapid release of the medicament at the initial stage of the dissolution test) of Preparations 2–4 were much smaller than that of Reference Preparation thereof.

Experiment 2

The incorporation efficiency of the medicament and the dissolution percentage at the first day after the starting of the dissolution test (the initial burst) were measured for the microspheres obtained in Example 10 and Reference Examples 6–9. The results are shown in Table 2.

TABLE 2

| | Incorporation Efficiency of Medicament and Initial Burst | | | |
|---|---|---|---|---|
| | Incorporation Efficiency | Initial Burst | Method for Preparation | Appearance of Oil Phase |
| Ex. 10 | 78.0% | 8.2% | Present Method (Solid Dispersion Method) | Clear |
| Ref. Ex. 6 | 57.1% | 10.4% | Suspension | Turbid |
| Ref. Ex. 7 | 67.7% | 13.7% | Ethanol-addition Method (10%) | Turbid |
| Ref. Ex. 8 | 57.9% | 10.1% | The same as above (20%) | Clear |
| Ref. Ex. 9 | 50.8% | 25.9% | The same as above (30%) | Clear |

As is clear from Table 2, although the incorporation efficiency of the medicament could be increased in the method comprising addition of an adequate amount of ethanol into oil phase, the present method was more efficient and effective in this point than those methods.

EFFECTS OF THE INVENTION

According to the present method, a sustained release microsphere preparation can be obtained by forming a solid dispersion having a water-soluble medicament dispersed in a biodegradable polymer homogeneously at molecular level, dissolving the solid dispersion into an oil phase, dispersing the oil phase in aqueous phase to give an oil in water (O/W) emulsion, and followed by removing solvent from the oil phase of the resulting emulsion. The microsphere preparation thus obtained shows higher incorporation efficiency of the medicament, and low initial burst, and hence, it is excellent and useful as a sustained release preparation of water-soluble medicament.

What is claimed is:

1. A method for producing a sustained release microsphere preparation, which comprises the steps of:

(1) dissolving a water-insoluble biodegradable polymer and a water-soluble pharmaceutically active ingredient in a solvent or solvents in which the water-insoluble biodegradable polymer and the water-soluble pharmaceutically active ingredient both can dissolved, (2) removing the solvent or solvents to form a solid dispersion of a water-soluble pharmaceutically active ingredient dispersed homogeneously in a water-insoluble biodegradable polymer, (3) dissolving the resulting solid dispersion in a water-immiscible organic solvent having a boiling point of below 100° C. to form a solution, (4) emulsifying the resulting solution (oil phase) into an aqueous phase to give an oil in water (O/W) emulsion, and (5) removing the water-immiscible organic solvent from the oil phase of the resulting emulsion to produce a sustained release microsphere preparation.

2. The method according to claim 1, wherein the water-immiscible organic solvent is selected from the group consisting of methylene chloride, chloroform, carbon tetrachloride and dichloroethane.

3. The method according to claim 1, wherein the water-immiscible organic solvent is methylene chloride.

4. The method according to claim 1, wherein the water-insoluble biodegradable polymer is selected from the group consisting of polylactic acid and lactic acid-glycolic acid copolymer.

5. The method according to claim 2, wherein the water-insoluble biodegradable polymer is selected from the group consisting of polylactic acid and lactic acid-glycolic acid copolymer.

6. A sustained release microsphere preparation produced according to the method of claim 1.

* * * * *

UNITED STATES PATENT AND TRADEMARK OFFICE
CERTIFICATE OF CORRECTION

PATENT NO.  : 5,556,642
DATED       : September 17, 1996
INVENTOR(S) : Masao KOBAYASHI et al.

It is certified that error appears in the above-indentified patent and that said Letters Patent is hereby corrected as shown below:

Title page, item [75], line 3, "Yashuhisa" should read --Yasuhisa--.

Claim 1, column 10, line 30, "dissolved," should read --dissolve,--.

Signed and Sealed this

Twenty-first Day of January, 1997

Attest:

BRUCE LEHMAN

*Attesting Officer*     *Commissioner of Patents and Trademarks*